US008953812B2

(12) United States Patent
Konchitsky

(10) Patent No.: US 8,953,812 B2
(45) **Date of Patent: *Feb. 10, 2015**

(54) VOICE SIGNALS IMPROVEMENTS IN COMPRESSED WIRELESS COMMUNICATIONS SYSTEMS

(71) Applicant: Alon Konchitsky, Santa Clara, CA (US)

(72) Inventor: Alon Konchitsky, Santa Clara, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 13/947,038

(22) Filed: Jul. 20, 2013

(65) Prior Publication Data

US 2013/0301844 A1 Nov. 14, 2013

Related U.S. Application Data

(63) Continuation-in-part of application No. 12/815,128, filed on Jun. 14, 2010, now Pat. No. 8,494,174, which is a continuation-in-part of application No. 12/176,297, filed on Jul. 18, 2008, now Pat. No. 7,817,808.

(60) Provisional application No. 60/950,813, filed on Jul. 19, 2007.

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04R 3/00*** | (2006.01) |
| ***H04R 1/40*** | (2006.01) |

(52) U.S. Cl.

CPC ................ *H04R 3/002* (2013.01); *H04R 1/406* (2013.01); *H04R 3/005* (2013.01); *H04R 2430/23* (2013.01); *H04R 2499/11* (2013.01)

USPC ........... 381/71.1; 381/94.1; 381/92; 381/110; 704/233; 704/E15.039; 708/322; 455/570

(58) Field of Classification Search

CPC ........ H04R 3/002; H04R 1/406; H04R 3/005; H04R 2499/11; H04R 2430/23; G10K 11/178; G10K 11/1788

USPC ......... 381/71.1, 94.1, 94.2, 94.7, 71.8, 71.11, 381/71.12, 92, 122, 91, 110; 455/570, 455/114.2; 704/214, 226, 233, 216, 217, 704/218, 200, E15.039; 708/322, 300, 422

See application file for complete search history.

(56) References Cited

U.S. PATENT DOCUMENTS 8,494,174 B2 * 7/2013 Konchitsky ................ 381/71.11

* cited by examiner

*Primary Examiner* — Vivian Chin
*Assistant Examiner* — Con P Tran
(74) *Attorney, Agent, or Firm* — Steven A. Nielsen; NielsenPatents.com

(57) ABSTRACT

Improvements in voice signals transmitted within communication systems are obtained by use of adaptive filters, front and rear microphones, noise cancelling systems and other means and methods. Disclosed embodiments include the use of directional microphones, primary inputs, secondary inputs, adaptive weight generators, canceller outputs to improve signal to noise ratios and other communication attributes.

18 Claims, 9 Drawing Sheets

VOICE SIGNALS IMPROVEMENTS IN COMPRESSED WIRELESS COMMUNICATIONS SYSTEMS

CROSS-REFERENCE TO A RELATED APPLICATION

This application is a continuation in part of U.S. patent application Ser. No. 12/815,128 filed on or about Jun. 14, 2010. The Ser. No. 12/815,128 U.S. patent application is a continuation in part and claims the priority date of parent application Ser. No. 12/176,297 filed on Jul. 18, 2008, which claims the benefit and priority date of U.S. provisional patent application 60/950,813 entitled "Dual Adaptive Structure for Speech Enhancement" filed on Jul. 19, 2007.

BACKGROUND

1. Field of the Invention

The present invention relates to means and methods of providing clear, high quality voice transmission signals with a high signal-to-noise ratio, in voice communication systems, devices, telephones, and other systems More specifically, the invention relates to systems, devices, and methods that automate control in order to correct for variable environment noise levels and reduce or cancel environmental noise prior to sending a voice communication over cellular telephone communication links.

2. Background of the Invention

Voice communication devices such as cell phones, wireless phones and devices other than cell phones have become ubiquitous; they show up in almost every environment. These systems and devices and their associated communication methods are referred to by a variety of names, including but not limited to, cellular telephones, cell phones, mobile phones, wireless telephones and devices such as Personal Data Assistants (PDA's) that include a wireless or cellular telephone communication capability. Such devices are used at home, office, inside a car, a train, at the airport, beach, restaurants and bars, on the street, and almost any other location. As to be expected, such diverse environments have relatively higher or lower levels of background, ambient, or environmental noise. For example, there is generally less noise in a quiet home as compared to a crowded bar or nightclub. If ambient noise, at sufficient levels, is picked up by a microphone, the intended voice communication degrades and though possibly not known to the users of the communication device, consumes more bandwidth or network capacity than is necessary, especially during non-speech segments in a two-way conversation when a user is not speaking.

A cellular network is a radio network made up of a number of radio cells (sometimes referred to as "cells") each served by a fixed transmitter, commonly known as a base station. The radio cells or cells cover different geographical areas in order to provide coverage over a wider geographical area than the area of one sole cell. Cellular networks are inherently asymmetric with a set of fixed main transceivers each serving a cell and a set of distributed (generally, but not always, mobile) transceivers which provide services to the network's users.

The primary requirement for a cellular network is that each of the distributed stations must distinguish signals from their own transmitter and signals from other transmitters. There are two common solutions to this requirement: Frequency Division Multiple Access (FDMA) and Code Division Multiple Access (CDMA). FDMA works by using a different frequency for each neighboring cell. By tuning to the frequency of a chosen cell, the distributed stations can avoid the signals from other neighbors. The principle of CDMA is more complex, but achieves the same result; the distributed transceivers can select one cell and listen to it. Other available methods of multiplexing such as Polarization Division Multiple Access (PDMA) and Time Division Multiple Access (TDMA) cannot be used to separate signals from one cell to the other since the effects of both vary with position, which makes signal separation practically impossible. Orthogonal Frequency Division Multiplexing (OFDM), in principle, consists of frequencies orthogonal to each other. TDMA, however, is used in combination with either FDMA or CDMA in a number of systems to give multiple channels within the coverage area of a single cell.

Wireless communication includes, but in not limited to two communication schemes: time based and code based. In the cellular mobile environment these techniques are named as TDMA (Time Division Multiple Access) which comprises, but not limited to the following standards GSM, GPRS, EDGE, IS-136, PDC, and the like; and CDMA (Code Division Multiple Access) which comprises, but not limited to the following standards: CDMA One, IS-95A, IS-95B, CDMA 2000, CDMA 1xEvDv, CDMA 1xEvDo, WCDMA, UMTS, TD-CDMA, TDS-DMA, OFDM, WiMax, WiFi, and others).

For the code division based standards or the orthogonal frequency division, as the number of subscribers grow and average minutes per month increase, more and more mobile calls typically originate and terminate in noisy environments. The background or ambient noise degrades the voice quality.

For the time based schemes, like GSM, GPRS and EDGE schemes, improving the end-users signal-to-noise ratio (SNR), improves the listening experience for users of existing TDMA based networks. This is done by improving the received speech quality by employing background noise reduction or cancellation at the sending or transmitting device.

Significantly, in an on-going cell phone call or other communication from an environment having relatively higher environmental noise, it is sometimes difficult for the party at the receiving end of the conversation to hear what the party in the noisy environment is saying. That is, the ambient or environmental noise in the environment often "drowns out" the cell phone user's voice, whereby the other party cannot hear what is being said or even if they can hear it with sufficient volume the voice or speech is not understandable. This problem may even exist in spite of the conversation using a high data rate on the communication network.

Attempts to solve this problem have largely been unsuccessful. Both single microphone and two microphone approaches have been attempted. For example, U.S. Pat. No. 6,415,034 to Hietanen et al patent describes the use of a second background noise microphone located within an earphone unit or behind an ear capsule. Digital signal processing is used to create a noise canceling signal which enters the speech microphone. Unfortunately, the effectiveness of the method disclosed in the Hietanen patent is compromised by acoustical leakage, that is where the ambient or environmental noise leaks past the ear capsule and into the speech microphone. The Hietanen patent also relies upon complex, power consuming, and expensive digital circuitry that may generally not be suitable for small portable battery powered devices such as pocket cellular telephones.

Another example is U.S. Pat. No. 5,969,838 (the "Paritsky patent") which discloses a noise reduction system utilizing two fiber optic microphones that are placed side-by-side next to one another. Unfortunately, the Paritsky patent discloses a system using light guides and other relatively expensive and/or fragile components not suitable for the rigors of cell phones and other mobile devices. Neither Paritsky nor Hietanen address the need to increase capacity in cell phone-based communication systems.

U.S. Pat. No. 5,406,622 to Silverberg et al uses two adaptive filters, one driven by the handset transmitter to subtract speech from a reference value to produce an enhanced reference signal; and a second adaptive filter driven by the enhanced reference signal to subtract noise from the transmitter. The Silverberg patent requires accurate detection of speech and non-speech regions. Any incorrect detection will degrade the performance of the system.

Previous approaches in noise cancellation have included passive expander circuits used in the electret-type telephonic microphone. These, however, suppress only low level noise occurring during periods when speech is not present. Passive noise-canceling microphones are also used to reduce background noise. These have a tendency to attenuate and distort the speech signal when the microphone is not in close proximity to the user's mouth; and further are typically effective only in a frequency range up to about 1 kHz.

Active noise-cancellation circuitry to reduce background noise has been suggested which employs a noise-detecting reference microphone and adaptive cancellation circuitry to generate a continuous replica of the background noise signal that is subtracted from the total background noise signal before it enters the network. Most such arrangements are still not effective. They are susceptible to cancellation degradation because of a lack of coherence between the noise signal received by the reference microphone and the noise signal impinging on the transmit microphone. Their performance also varies depending on the directionality of the noise; and they also tend to attenuate or distort the speech.

Thus, there is a need in the art for a method of noise reduction or cancellation that is robust, suitable for mobile use, and inexpensive to manufacture. The increased traffic in cellular telephone based communication systems has created a need in the art for means to provide a clear, high quality signal with a high signal-to-noise ratio. The requirements of a noise reduction system for speech enhancement include but are not limited to intelligibility and naturalness of the enhanced signal, improvement of the signal-to-noise ratio, short signal delay, and computational simplicity There are several methods for performing noise reduction, but all can be categorized as types of filtering. In the related art, speech and noise are mixed into one signal channel, where they reside in the same frequency band and may have similar correlation properties. Consequently, filtering will inevitably have an effect on both the speech signal and the background noise signal. Distinguishing between voice and background noise signals is a challenging task. Speech components may be perceived as noise components and may be suppressed or filtered along with the noise components.

Even with the availability of modern signal-processing techniques, a study of single-channel systems shows that significant improvements in SNR are not obtained using a single channel or a one microphone approach. Surprisingly, most noise reduction techniques use a single microphone system and suffer from the shortcoming discussed above.

One way to overcome the limitations of a single microphone system is to use multiple microphones where one microphone may be closer to the speech signal than the other microphone. Exploiting the spatial information available from multiple microphones has lead to substantial improvements in voice clarity or SNR in multi-channel systems. However, the current multi-channel systems use separate front-end circuitry for each microphone, and thus increase hardware expense and power consumption.

Hence, there is a room in the art for new means and methods of increasing SNR in hand-held devices that capture sound with multiple microphones but use the circuitry or hardware of a single channel system. Adaptive noise cancellation is one such powerful speech enhancement technique based on the availability of an auxiliary channel, known as reference path, where a correlated sample or reference of the contaminating noise is present. This reference input is filtered following an adaptive algorithm, in order to subtract the output of this filtering process from the main path, where noisy speech is present.

As with any system, the two microphone systems also suffer from several shortfalls. The first shortfall is that, in certain instances, the available reference input to an adaptive noise canceller may contain low-level signal components in addition to the usual correlated and uncorrelated noise components. These signal components will cause some cancellation of the primary input signal. The maximum signal-to-noise ratio obtained at the output of such noise cancellation system is equal to the noise-to-signal ratio present on the reference input.

The second shortfall is that, for a practical system, both microphones should be worn on the body. This reduces the extent to which the reference microphone can be used to pick up the noise signal. That is, the reference input will contain both signal and noise. Any decrease in the noise-to-signal ratio at the reference input will reduce the signal-to-noise ratio at the output of the system. The third shortfall is that, an increase in the number of noise sources or room reverberation will reduce the effectiveness of the noise reduction system.

SUMMARY OF THE INVENTION

The present invention provides a novel system and method for monitoring the noise in the environment in which a cellular telephone is operating and cancels the environmental noise before it is transmitted to the receiving party so as to allow the receiving on the other end of the voice communication link to more easily hear and determine what the cellular telephone user is transmitting.

The present invention preferably employs noise reduction and/or cancellation technology that is operable to attenuate or even eliminate pre-selected portions of an audio spectrum. By monitoring the ambient or environmental noise in the location in which the cellular telephone is operating and applying noise reduction and/or cancellation protocols at the appropriate time via analog and/or digital signal processing, unexpected results are achieved as it is possible to significantly reduce the ambient or background noise to which a party to a cellular telephone call might be subjected.

In one aspect of the invention, the invention provides a system and method that enhances the convenience of using a cellular telephone or other wireless telephone or communications device, even in a location having relatively loud ambient or environmental noise.

In another aspect of the invention, the invention provides a system and method for canceling ambient or environmental noise before the ambient or environmental noise is transmitted to the receiving party.

In yet another aspect of the invention, the invention monitors ambient or environmental noise via a second microphone associated with a cellular telephone, which is different from a first microphone primarily responsible for collecting the speaker's voice, and thereafter cancel the monitored environmental noise.

In still another aspect of the invention, an enable/disable switch is provided on a cellular telephone device to enable/disable the noise reduction.

These and other aspects of the present invention will become apparent upon reading the following detailed description in conjunction with the associated drawings. The present invention overcomes shortfalls in the related art and achieves unexpected results by, among other methods, combining a directional microphone solution with an adaptive noise cancellation algorithm. Economies in hardware and power consumption are obtained by two microphones sharing the front-end hardware. These and other aspects and advantages will be made apparent when considering the following detailed descriptions taken in conjunction with the associated drawings.

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

The present invention provides a novel and unique background noise or environmental noise reduction and/or cancellation feature for a communication device such as a cellular telephone, wireless telephone, cordless telephone, recording device, a handset, and other communications and/or recording devices. While the present invention has applicability to at least these types of communications devices, the principles of the present invention are particularly applicable to all types of communication devices, as well as other devices that process or record speech in noisy environments such as voice recorders, dictation systems, voice command and control systems, and similar systems. For simplicity, the following description employs the term "telephone" or "cellular telephone" as an umbrella term to describe various embodiments of the present invention, but those skilled in the art will appreciate the fact that the use of such "term" is not considered limiting to the scope of the invention, which is set forth by the claims.

Hereinafter, preferred embodiments of the invention will be described in detail in reference to the accompanying drawings. It should be understood that like reference numbers are used to indicate like elements even in different drawings. Detailed descriptions of known functions and configurations that may unnecessarily obscure an aspect of the invention have been omitted.

Figure 1:
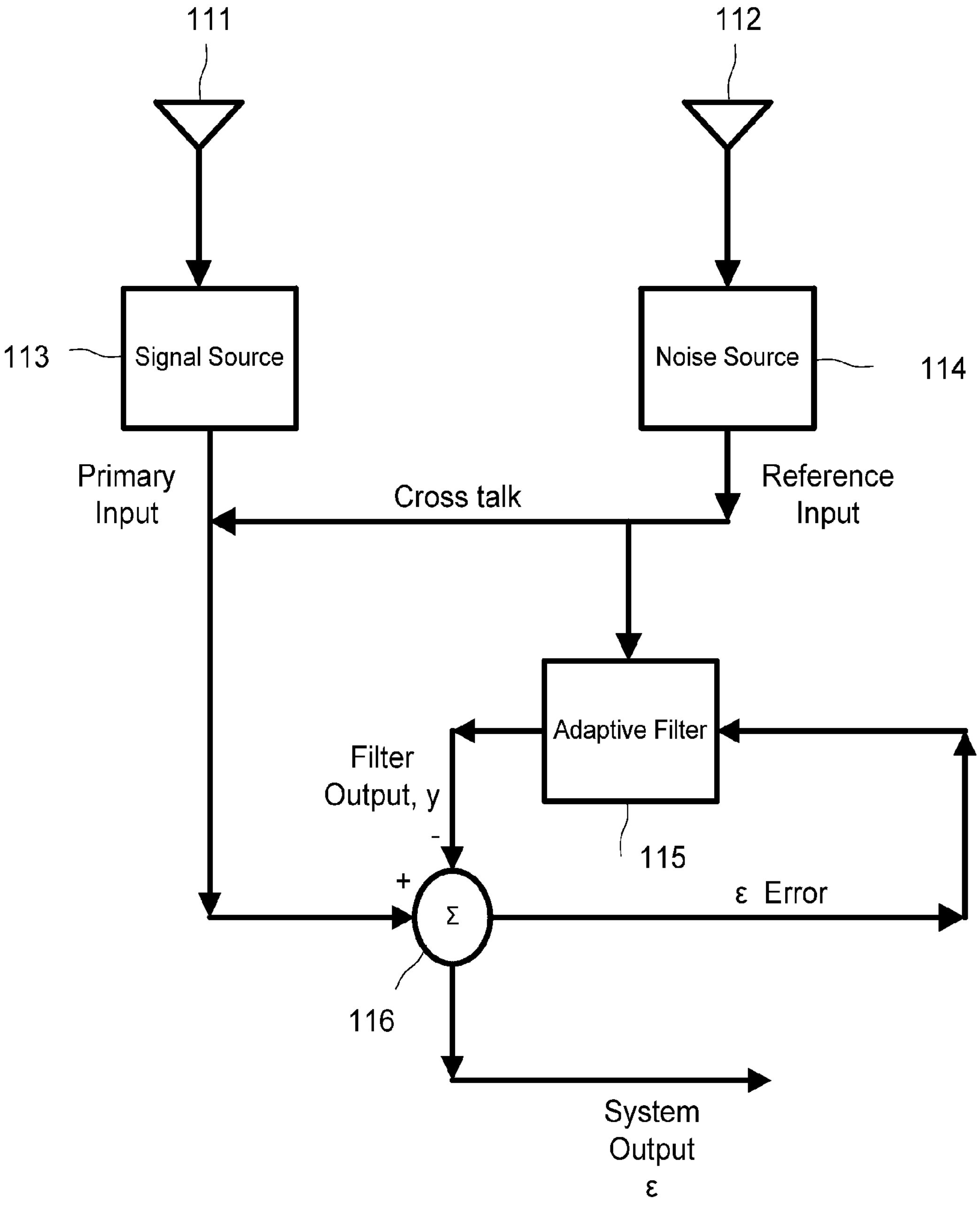
FIG. 1 PRIOR ART
FIG. 1 is diagram of an exemplary prior art embodiment of a basic adaptive noise canceller with noise components leaking into the primary input.

In FIG. 1 an example of the prior art is shown wherein, block 111 is the primary microphone and 112 is the reference microphone. 113 and 114 are the signal source and noise source respectively. The primary input is given by $$\text{Primary input}=s+n \tag{1}$$

A second sensor receives a noise n1 which is uncorrelated with the signal but correlated with some unknown way with the noise n. This sensor provides the "reference input", 114, to the canceller.

$$\text{Secondary input signal}=n1 \tag{2}$$

Block 115 adaptively filters the noise n1, to produce an output y that is a close replica of n. Block 116 subtracts the adaptive filter output, y, from the primary input, s+n, to produce the system output, given by, s+n−y.

$$\text{Output}=\epsilon=s+n-y \tag{3}$$

Squaring equation (3), we get:

$$\epsilon^2=s^2+(n-y)^2+2s(n-y) \tag{4}$$

Taking the expectation of both sides of the above equation and assuming s is uncorrelated with n and with y, yields $$E[\epsilon^2]=E[s^2]+E[(n-y)^2] \tag{5}$$

$$E_{min}[\epsilon^2]=E_{min}[s^2]+E_{min}[(n-y)^2] \tag{6}$$

When the filter is adjusted so that E $[\epsilon^2]$ is minimized, E $[(n-y)^2]$ is also minimized. Since signal in the output remains constant, minimizing the total output power maximizes the output signal-to-noise ratio. The filter output, y, is then a best least-squares estimate of the primary noise n. When the reference input is completely uncorrelated with the primary input, the filter will turn off and will not increase output noise.

Figure 2:
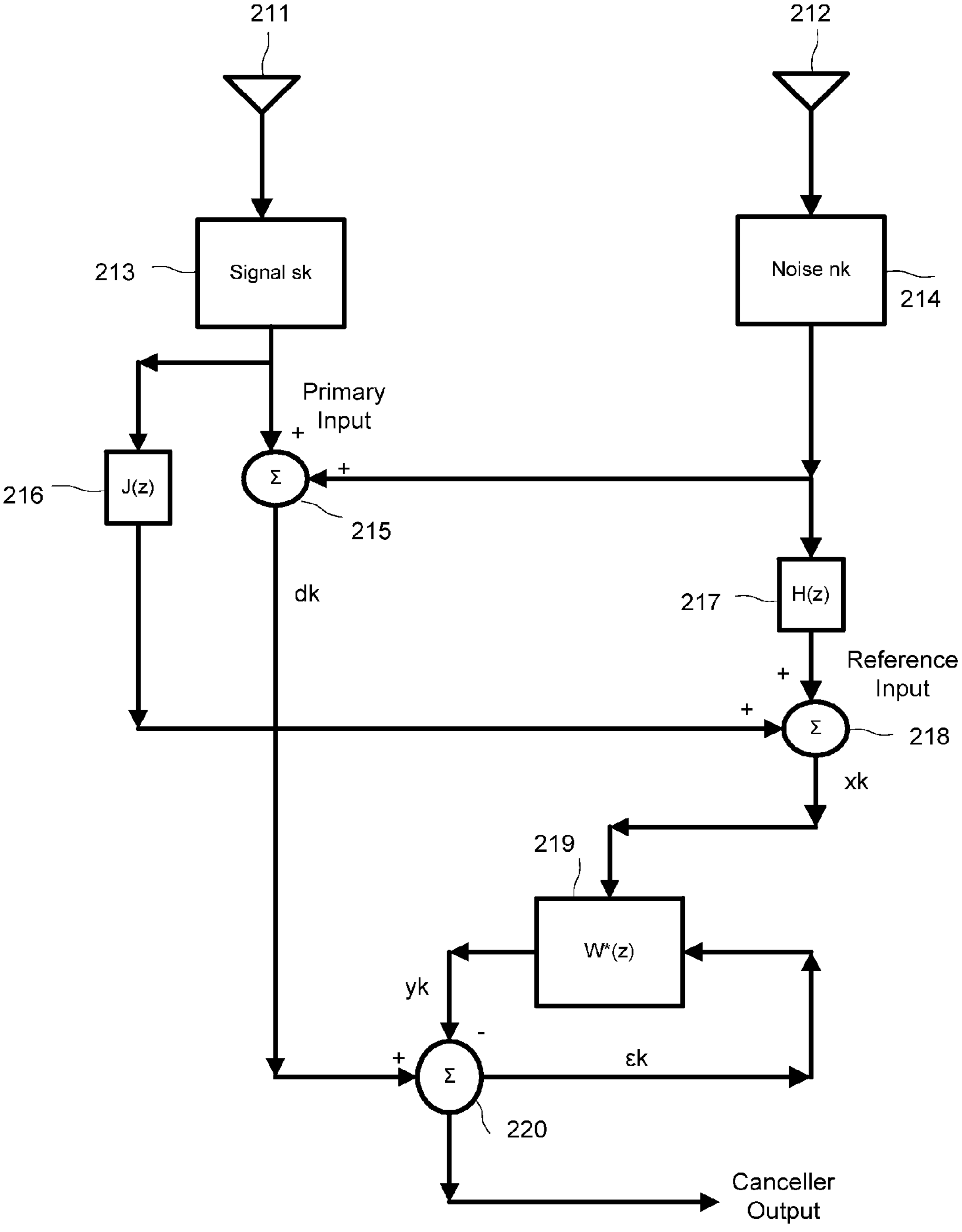
FIG. 2 PRIOR ART
FIG. 2 is diagram of an exemplary prior art embodiment of a basic adaptive noise canceller with noise components leaking into the primary input and signal components leaking into the reference input.

In real-time communication systems, the signal and noise received at the two microphones are mutually correlated due to cross-talk. In FIG. 2, 211 is the primary microphone and 212 is the secondary microphone. Blocks 213 and 214 are signal source, sk and noise source, nk respectively. The signal components leaking into the reference input are assumed to be propagated through a channel with transfer function J(z). Block 216 represents this transfer function. Similarly, the noise component received by the second microphone is assumed to be propagated through a channel with a transfer function H(z). Block 217 represents this transfer function.

At 218, the noise, nk through H(z) and signal, sk through J(z) are added to produce the reference input. At 215, the signal, sk and noise, nk are directly added to produce primary input. Block 219 is an adaptive weight generator. The reference input is multiplied using these adaptive weights. Block 220 subtracts the output of the 219 from the primary input to get the canceller output. Assuming the adaptive solution to be unconstrained and the noise at primary and reference inputs to be mutually correlated, the signal-to-noise density ratio at the noise canceller output is simply the reciprocal at all frequencies of the signal-to-noise density ratio at the reference input. The process is called power inversion [2].

$$\rho_{out}(z) = \frac{1}{\rho_{ref}(z)} \tag{7}$$

Where $$\rho_{ref}(z) = \frac{\phi_{ss}(z)|J(z)|^2}{\phi_{nn}(z)|H(z)|^2}$$

is the signal-to-noise density ratio at the reference input. $\phi_{ss}$ and $\phi_{nn}$ are the spectra of signal component and noise component in the reference input. The signal-to-noise density ratio at the primary input is given by, $$\rho_{pri}(z) = \frac{\phi_{ss}(z)}{\phi_{nn}(z)} \tag{8}$$

The signal distortion D(z) is defined as a dimensionless ratio of the spectrum of the output signal component propagated through the adaptive filter in to the spectrum of the signal component at the primary input.

$$D(z) = \left|\frac{J(z)}{H(z)}\right|^2 \tag{9}$$

Using the equations for $\rho_{ref}(z)$ and $\rho_{pri}(z)$, the signal distortion D(z) of equation (9) can be rewritten as:

$$D(z) = \frac{\rho_{ref}(z)}{\rho_{pri}(z)} \tag{10}$$

With unconstrained adaptive solution and mutually correlated noise at primary and reference inputs, low signal distortion results from a high signal-to-noise density ratio at the primary input and a low signal-to-noise density ratio at the reference input. This conclusion is intuitively reasonable.

Widrow's LMS-algorithm has been used extensively in all types of applications but only few people proposed a solution to the signal leakage problem. In some speech applications, a partial solution can be provided by using a signal triggered switch to stop adaptation during periods of speech when the effect of leakage becomes harmful. The present invention combines the adaptive noise cancellation algorithm with the adaptive directional microphone system.

Figure 3:
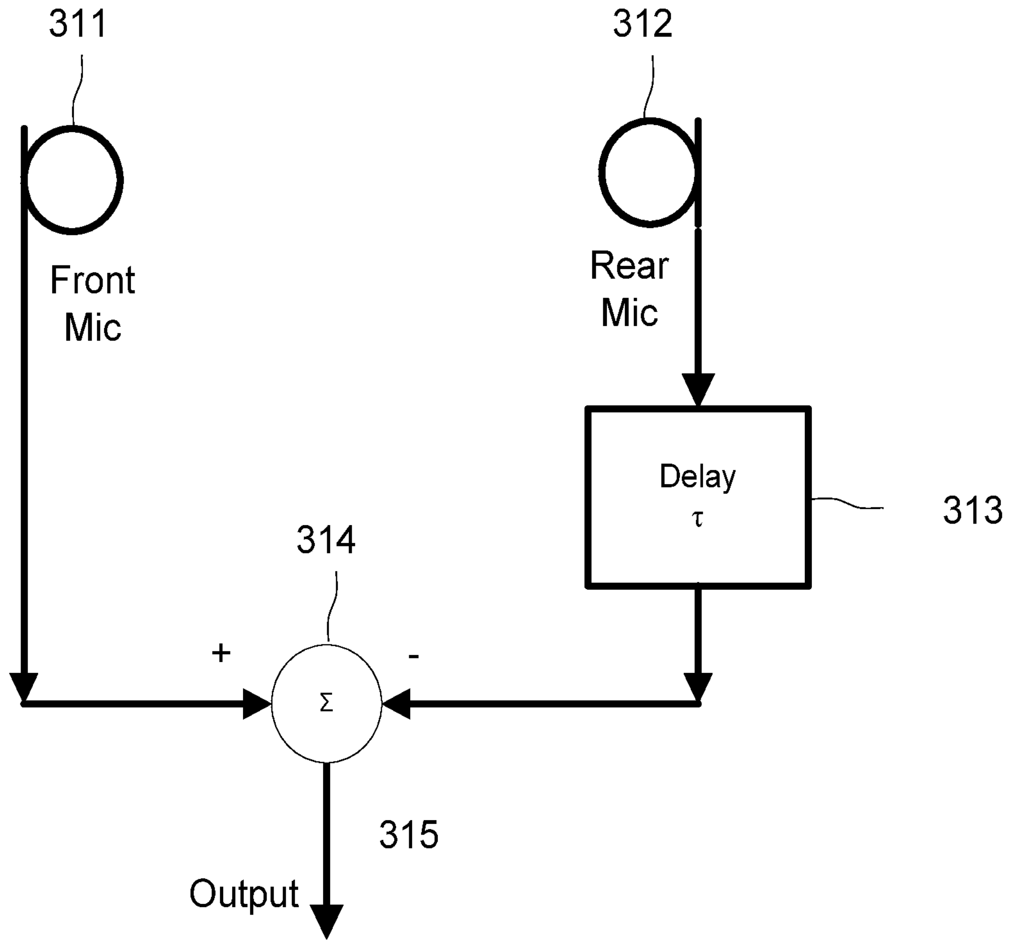
FIG. 3 PRIOR ART
FIG. 3 is diagram of an exemplary prior art embodiment of a system which makes two omni directional microphones directional using one delay element.

The most common technique in use in hearing aids is a directional microphone or a dual-omni microphone system with some fixed polar patterns, as shown in FIG. 3. The directional system in FIG. 3 can provide different polar patterns by selecting different values of delay $\tau$. For a system with two near by microphones, in end fire orientation, the direct way to achieve adaptive directionality is to adaptively change the delay $\tau$ so that its value is equal to the transmission delay value of the noise between the two microphones. In FIG. 3, blocks 311 and 312 are the front and back microphones respectively. Block 313 is a delay element which delays the signal from back microphone. The delayed back microphone signal is subtracted from the front microphone signal. Block 314 does this subtraction. The output of this subtraction is a directional signal, 315.

As an example consistent with the principles of the invention, FIGS. **4*a*, 4*b* and 4*c*** show three polar patterns with the value of delay $\tau$ being 0, 0.5T and T, where T is the propagation time between the two microphones.

$$T=d/c \tag{11}$$

where d is the distance between two microphones and c is the speed of sound in air. The direction directly in front of the hearing-aid wearer is represented as 0°, and 180° represents the direction directly behind the wearer. The plots show the gain as a function of direction of sound arrival where the gain from any given direction is represented by the distance from the center of the circle. These polar patterns are called bi-directional pattern (with null at 90° and 270°), hyper-cardioid pattern (with null at 120° and 240°) and cardioid pattern (with null at 180°). Various polar patterns can be obtained by varying $\tau$ between 0 and T.

Obviously, the cardioid system attenuates sound the most from directly behind the wearer, where as the bidirectional system attenuates the noise coming from 90° and 270° with respect to the speaker. In different listening environments, users select one of these three polar patterns using control buttons to achieve the best noise reduction performance, given the specific listening environment. However, for time-varying and moving-noise environments, this fixed directional system delivers degraded performance. Therefore, a system with adaptive directionality is highly desirable.

Figure 4A:
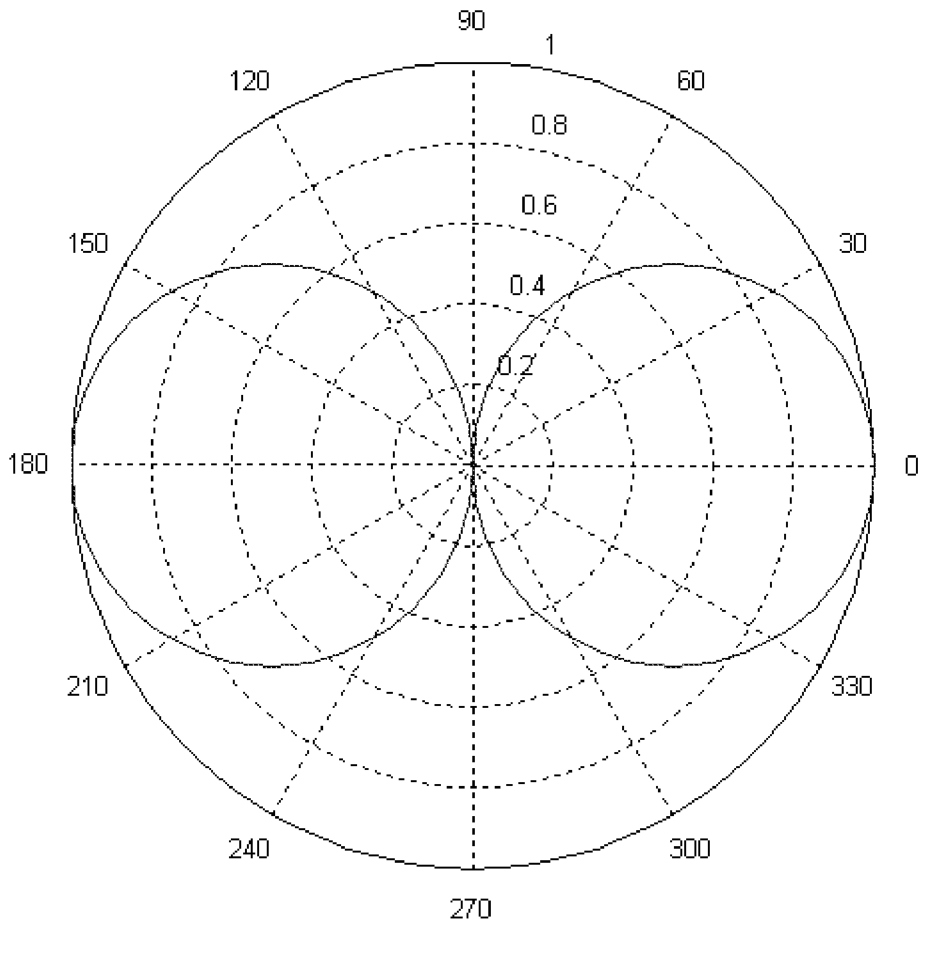
FIG. 4a PRIOR ART
FIG. 4*a* is diagram of an exemplary embodiment of prior art showing the bi-directional polar pattern obtained by subtracting the rear microphone from the front microphone without any delay ($\tau=0$).
Figure 4B:
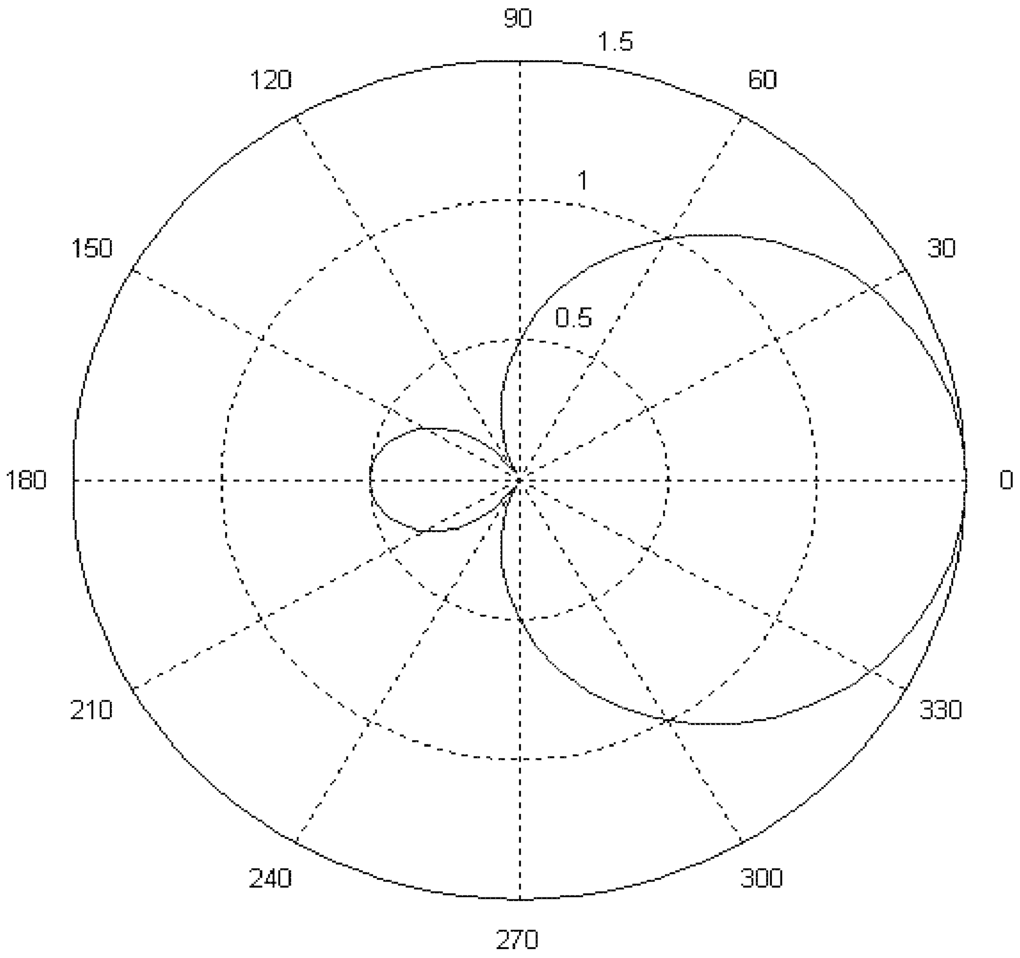
FIG. 4b PRIOR ART
FIG. 4*b* is diagram of an exemplary embodiment of related art showing the hyper-cardioid polar pattern obtained by subtracting the rear microphone from the front microphone with a delay $\tau=0.5T$.
Figure 4C:
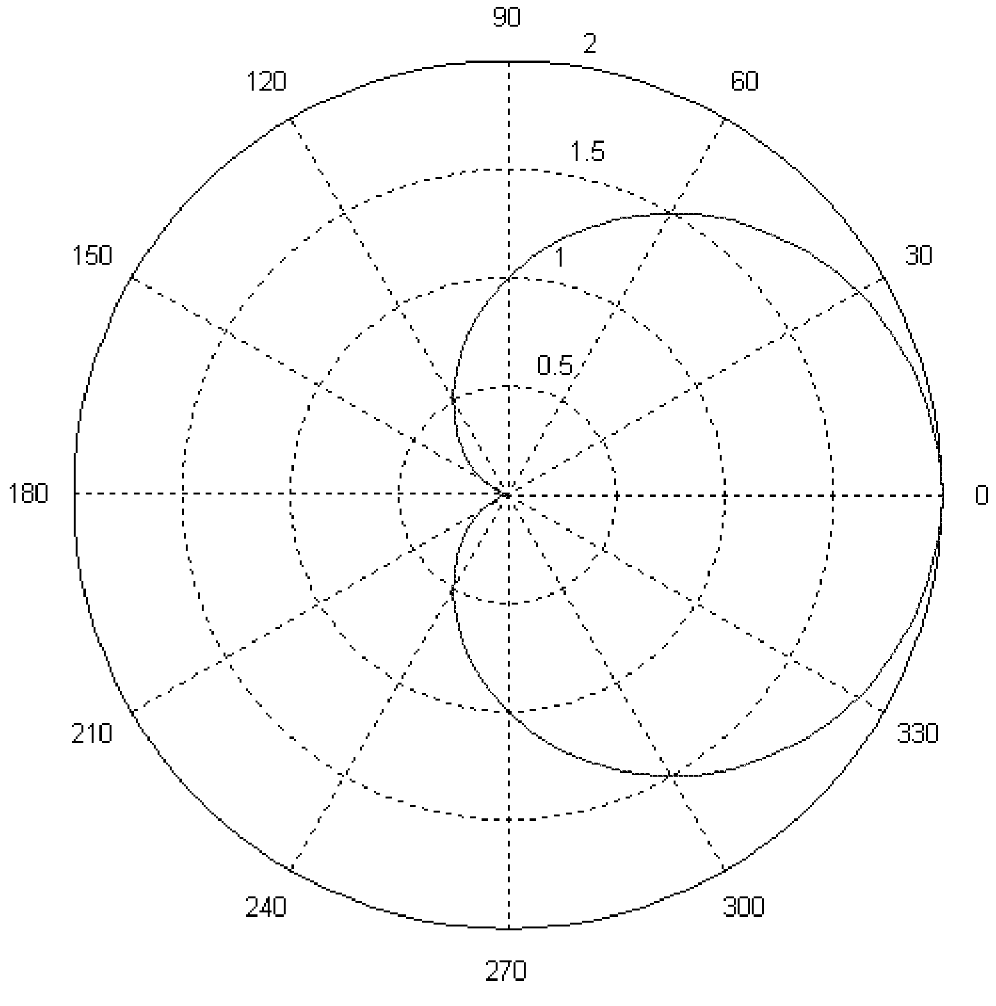
FIG. 4c PRIOR ART
FIG. 4*c* is diagram of an exemplary embodiment of prior art showing the cardioid polar pattern obtained by subtracting the rear microphone from the front microphone with a delay $\tau=T$.

FIG. **4*a* shows an implementation wherein the polar pattern obtained when the rear microphone signal (without any delay) is subtracted from the front microphone signal. In this configuration, any signal coming from 90° and 270° are totally cancelled out. FIG. 4*b* shows the polar pattern obtained when the rear microphone signal is delayed by 0.5T. For a sampling frequency of 8000 Hz, this delay is half sample. In this configuration, any signal coming from 120° and 240° are totally cancelled out. FIG. 4*c*** shows the polar pattern obtained when the rear microphone signal is delayed by T. For a sampling frequency of 8000 Hz, this delay is one sample. In this configuration, any signal coming from 180° is totally cancelled out.

Figure 5:
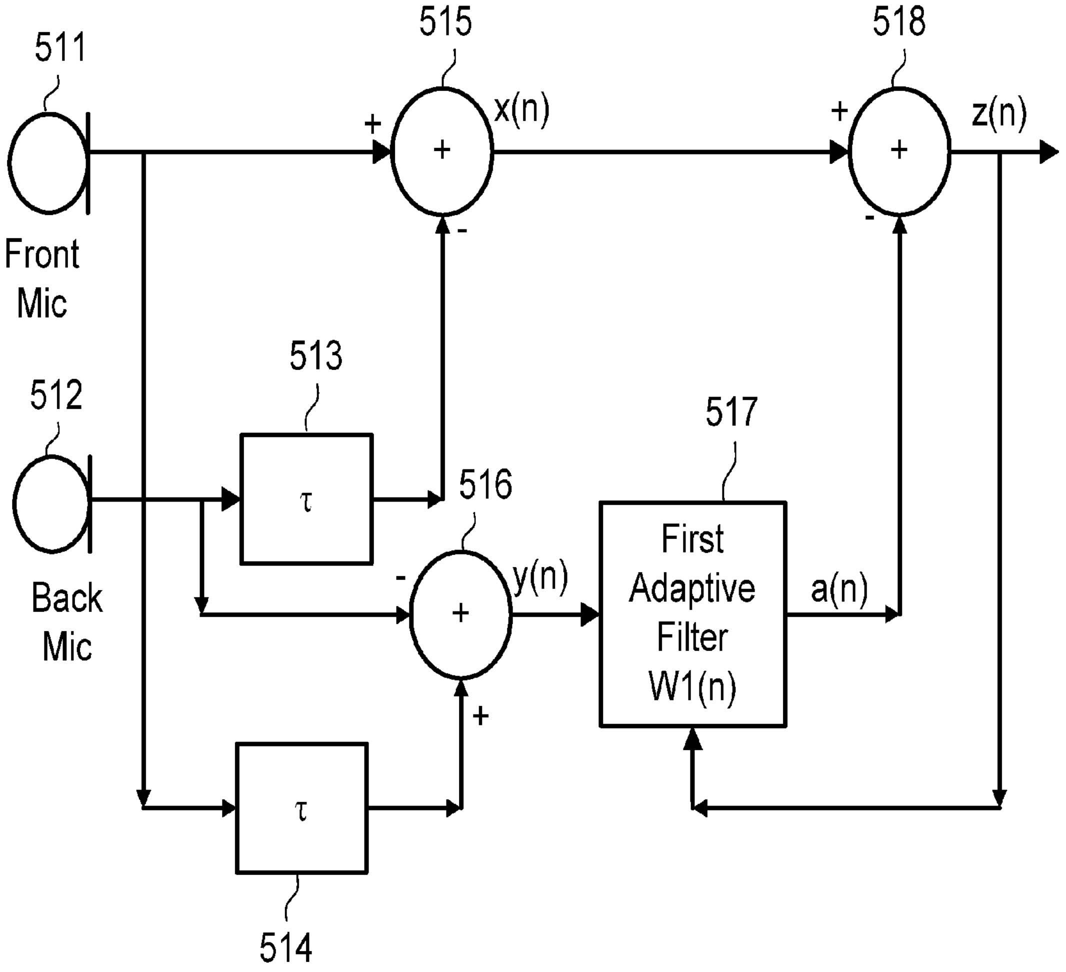
FIG. 5 is diagram of an exemplary embodiment showing the adaptive directional microphone system consistent with the principles of the present invention.

An adaptive directionality system, consistent with the principles of the invention as shown in FIG. 5, is implemented with two nearby microphones. This system is based mainly on an adaptive combination of two fixed polar patterns that are arranged to make the null of the combined polar pattern of the system output always be toward the direction of the noise. In FIG. 5, 511 and 512 are the front and back microphones respectively. Block 513 is a delay element where the back microphone signal is delayed by $\tau$ (one sample for 8 kHz sampling rate). Block 515 subtracts the output of block 513 from the front microphone signal to give a cardioid, x(n), with a null at 180°. Block 514 is a delay element where the front microphone signal is delayed by $\tau$ (one sample for 8 kHz sampling rate). Block 516 subtracts the rear microphone signal from this delayed front microphone signal to give a cardioid, y(n), with a null at 0°.

Block 517 is an adaptive filter which generates adaptive weights. The signal y(n) is filtered using this adaptive filter $W_1(z)$ to give the output a(n). Block 518 subtracts the output of the adaptive filter from x(n) to give a highly directional signal, z(n). The filter coefficients are adaptively estimated to minimize the power of the interfering noise. The polar pattern of the whole system output z (n) is a combination of x (n) and y (n) and determined by the filter $W_1(z)$. Assuming $W_1(z)$. is linear, discrete and designed to be optimal in the minimum mean square error sense a Wiener solution is applicable. In general the Wiener-Hopf equation applies:

$$W=R^{-1}P$$

Where W is the filter coefficient vector, R is the correlation matrix of y and P is the cross-correlation vector between x and y.

$$W = \begin{bmatrix} w0 \\ w1 \\ w2 \\ \dots \\ \dots \\ wp \end{bmatrix} \quad R = [YY^T] \quad P = [XY]$$

Figure 6:
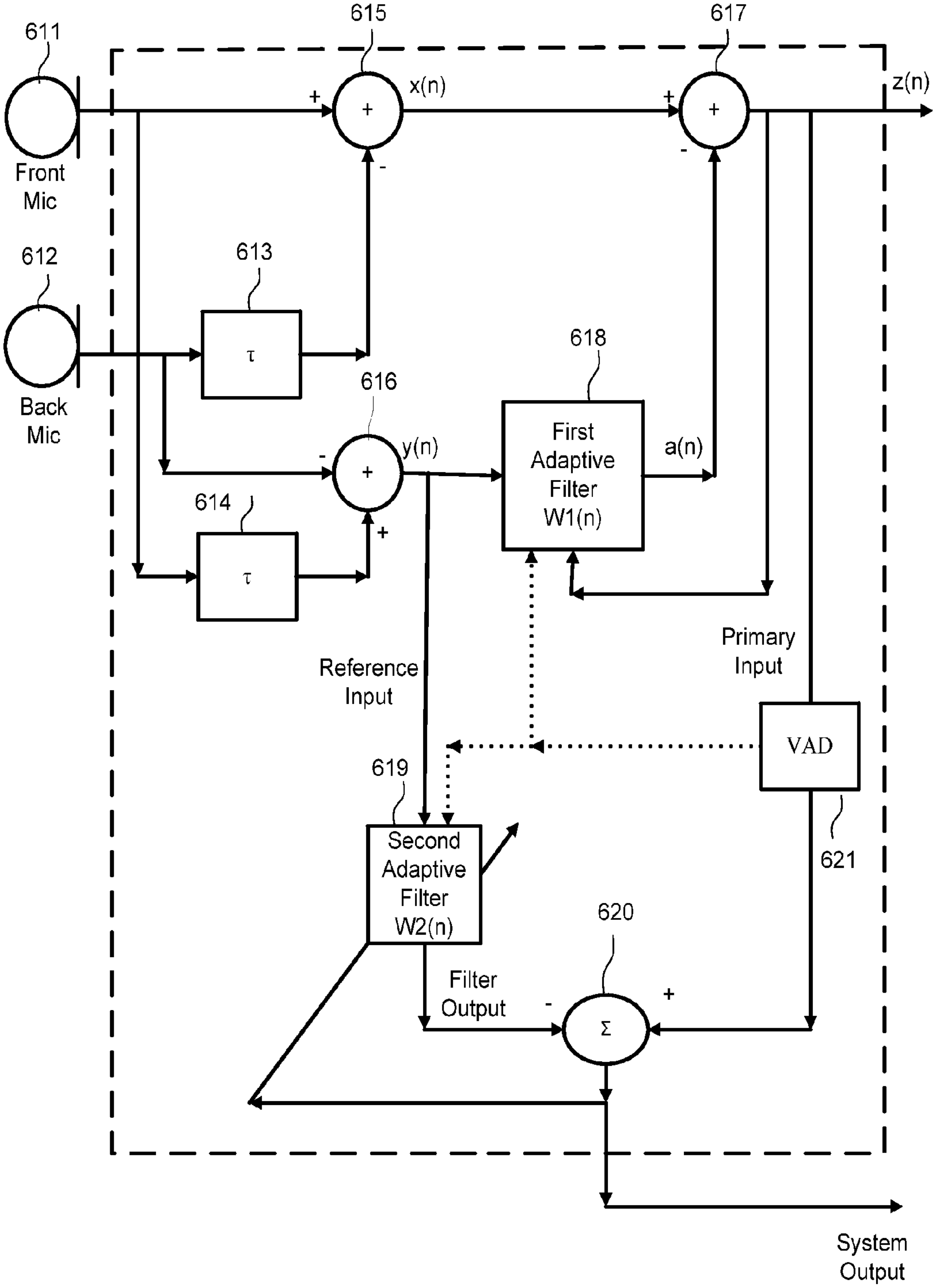
FIG. 6 is diagram of an exemplary embodiment consistent with the principles of the present invention that combines an adaptive directional microphone system with an adaptive noise canceling system.

The Wiener solution can be approximated by well know techniques as Least Mean Squares. In this invention, the adaptive directionality microphone system is combined with adaptive noise cancellation system as shown in FIG. 6. In FIG. 6, 611 and 612 are the front and back microphones respectively. Block 613 is a delay element where the back microphone signal is delayed by τ (one sample for 8 kHz sampling rate). Block 615 subtracts the output of block 613 from the front microphone signal to give a cardioid, x(n), with a null at 180°. Block 614 is a delay element where the front microphone signal is delayed by τ (one sample for 8 kHz sampling rate). Block 616 subtracts the rear microphone signal from this delayed front microphone signal to give a cardioid, y(n), with a null at 0°.

Block 618 is an adaptive filter which generates adaptive weights. The signal y(n) is filtered using this adaptive filter $W_1(z)$ to give the output a(n). Block 617 subtracts the output of the adaptive filter from x(n) to give a highly directional signal, z(n). Block 619 is a second adaptive filter. The signal y (n) is given as a reference input to the second adaptive filter $W_2(z)$. Block 621 is a Voice Activity Detector (VAD) which identifies the speech and non-speech regions of the directional signal z(n). This signal is given as the primary input to the second adaptive filter which produces an output similar to the noise that is left over in z (n). Block 620 subtracts the adaptive filter output from the directional signal z (n) to remove any residual noise.

Figure 7:
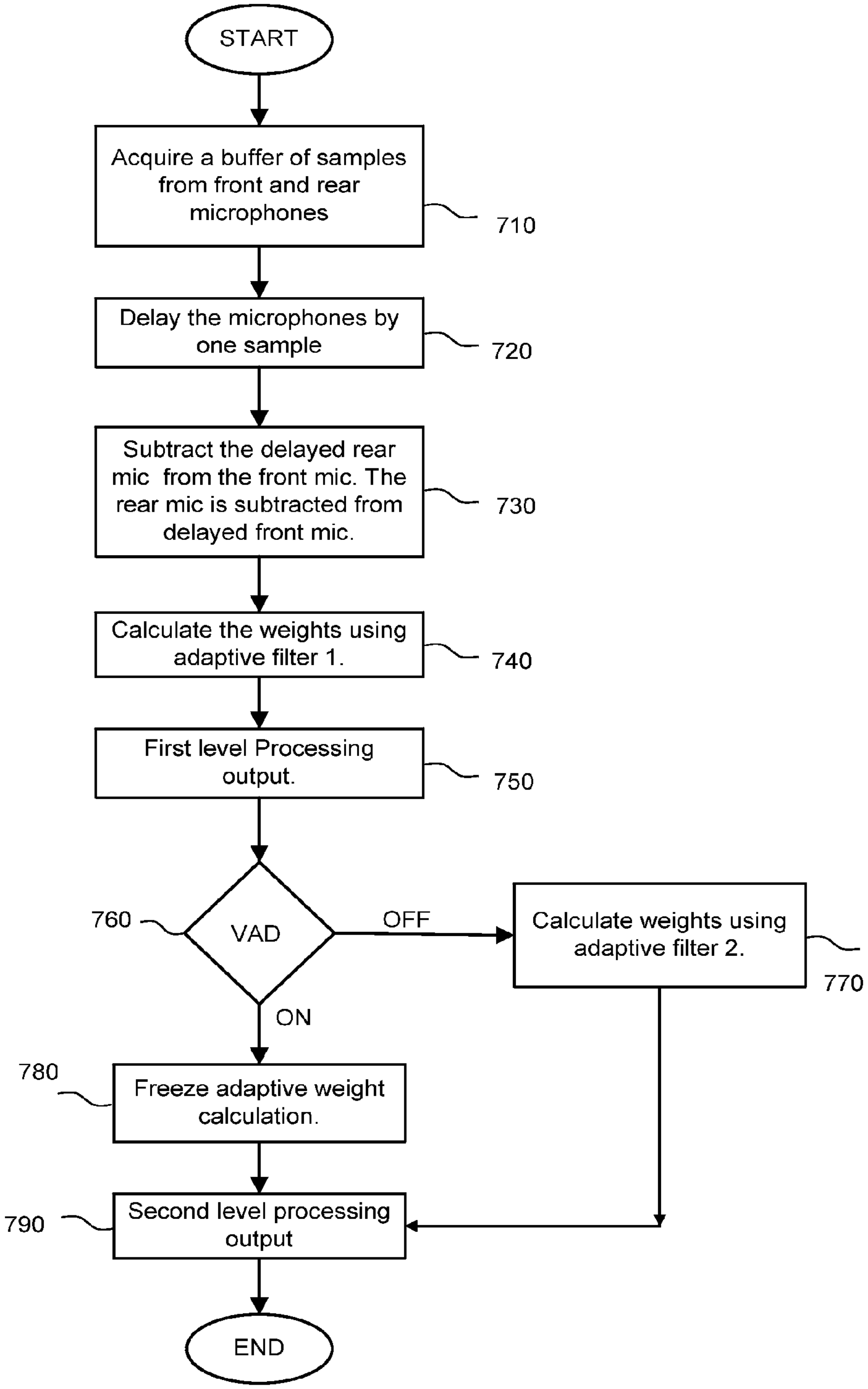
FIG. 7 is a flow chart describing an embodiment of the present invention.

FIG. 7 is a flowchart describing principles of the invention. At block 710, the front and rear microphones, read a buffer of 160 samples. The distance between the two microphones is 4 cm. The time delay, T, between the two microphones is given by:

$$T=d/c$$

Where c is the speed of sound in air (320 m/s). For a sampling frequency of 8000 Hz, the propagation delay between the two microphones is one sample. At block 720, the signals are delayed by one sample. At block 730, the delayed rear microphone signal is subtracted from the front microphone signal. The delayed front microphone signal is subtracted from the rear microphone signal. At block 740, the weights are calculated adaptively. The weights are calculated as a ratio of the cross-correlation between the two microphones, $R_{xy}$, and the auto-correlation of the rear microphone, $R_{yy}$. The auto-correlation and cross-correlation are averaged for smoothing purposes. The averaging is done as shown below:

$$W_{opt} = \frac{R_{xy}}{R_{yy}}$$

$$R_{xy} = \alpha R_{xy\_prev} + (1-\alpha)R_{xy}$$

$$R_{yy} = \alpha R_{yy\_prev} + (1-\alpha)R_{yy}$$

The value of α can be chosen to be in the range 0.75 to 0.95.

At 750, the output of the adaptive filter is subtracted from the signal obtained by subtracting the delayed rear microphone signal from the front microphone signal. This gives the output of the first level of processing. At block 760, the Voice Activity Detector (VAD) determines speech and non-speech regions. The VAD controls the two adaptive filters. During non-speech regions (VAD=OFF), the weights are updated at block 770. During speech regions (VAD=ON), the weights are frozen, 780. The adaptive filter 2, block 770 receives two inputs. One is the output of the first processing level. The other input is the signal obtained by subtracting the rear microphone signal from the delayed front microphone signal. Block 790 does the second level of processing. Here the residual noise left over from the first processing level is removed.

As described hereinabove, the invention has the advantages of improving the signal-to-noise ratio by reducing noise in various noisy conditions, enabling the conversation to be pleasant. While the invention has been described with reference to a detailed example of the preferred embodiment thereof, it is understood that variations and modifications thereof may be made without departing from the true spirit and scope of the invention. Therefore, it should be understood that the true spirit and the scope of the invention are not limited by the above embodiment, but defined by the appended claims and equivalents thereof.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

All the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

The disclosed embodiments of the invention include, but are not limited to, the following items:

Item 1. A method of improving the signal to noise ratio in a communication system, the method comprising:

acquiring one or more buffers of sound samples from a back microphone and a front microphone, resulting in a back microphone signal and a front microphone signal;

applying a propagation delay between the two microphones for a length of time equal to one sample, resulting in a delayed back microphone signal and a delayed front microphone signal;

subtracting the delayed back microphone signal from the front microphone signal;

subtracting the back microphone signal from the delayed front microphone signal;

using a first adaptive filter, the first adaptive filter calculating weights adaptively, as the ratios of the cross-correlation between the two microphones Rxy, and the auto-correlation of the back microphone, Ryy, and averaging the auto-correlation and cross-correlation for smoothing purposes;

subtracting the output of the first adaptive filter from a signal obtained by subtracting the delayed back microphone signal from the front microphone signal, giving a first level of output processing;

using a voice activity detector to determine speech and non-speech regions and to control the first adaptive filter and a second adaptive filter;

during non-speech regions, the voice activity detector is in an off position and weights of the second adaptive filter are updated, and the second adaptive filter receives a signal obtained by subtracting the back microphone signal from the delayed front microphone signal, the output from the second adaptive filter is sent to a second level processing unit;

during speech regions, the voice activity detector is in an on position and freezes adaptive weight calculations and sends the resulting output to the second level processing unit; and the second level processing unit removes residual noise left over from the first processing level.

[Item 2] The method of item 1 wherein the averaging of the auto-correlation and cross-correlation is achieved by the following equation:

$$W_{opt} = \frac{R_{xy}}{R_{yy}}$$

$$R_{xy} = \alpha R_{xy\_prev} + (1-\alpha)R_{xy}$$

$$R_{yy} = \alpha R_{yy\_prev} + (1-\alpha)R_{yy}$$

and the value of a can be chosen to be in the range 0.75 to 0.95.

[Item 3] An adaptive directionality microphone system, the system comprising:

a back microphone sends input into a delay element wherein the back microphone signal delayed by a unit of time t;

a cardioid x(n) component subtracts output of a rear microphone signal from the output of the delay element to give cardioid signal, y(n), with a null at 0°;

cardioids signal y(n) is filtered using a first adaptive filter W1(z) which generates adaptive weights, to give an output a(n);

a subtraction component subtracts the output of the first adaptive filter from x(n) to give a directional signal, z(n)

[Item 4] The system of Item 3 wherein the filter coefficients are adaptively estimated to minimize the power of the interfering noise.

[Item 5] The system of item 3 wherein the polar pattern of the system output z(n) is a combination of x(n) and y(n) and determined by the filter W1(z).

[Item 6] The adaptive directionality microphone system of claim 5 combined with an adaptive noise cancellation system, the adaptive noise cancellation system comprising:

the signal from the back microphone is delayed by a time period of one sample and the resulting signal is subtracted from the front microphone signal to produce a cardioid, x(n) with a null at 1800;

the signal from the front microphone is delayed by the time period of one sample, to produce a delayed front microphone signal, the rear microphone signal is subtracted from the delayed front microphone signal to produce a cardioid, y(n) with a null at 00;

the signal y(n) is filtered using a first adaptive filter W1(z) to give an output a(n);

the output of the first adaptive filter is subtracted from the signal x(n) to produce directional signal z(n);

signal y(n) is given as a reference input to a second adaptive filter W2(n);

a voice activity detector detects speech and non-speech regions of directional signal z(n), and the signal is given as the primary input to the second adaptive filter which in turn produces an output similar to the noise that remains in the z(n) signal; and output from the second adaptive filter is subtracted from directional signal z(n).

Disclosed means and methods include the following points

Point 1. A method of improving signal quality in a voice communication system, the method comprising:

a) receiving one or more buffers of sound samples from a first microphone and a second microphone, resulting in a first microphone signal and a second microphone signal;

b) processing the first microphone signal and the second microphone signal to obtain a cardioid shape output signal;

c) obtaining a first cardioid shape signal by subtracting a delayed second microphone signal from the first microphone signal, the delayed second microphone signal obtained from the second microphone;

d) obtaining a second cardioid shape signal by subtracting the second microphone signal from a delayed first microphone signal, the delayed first microphone signal obtained from the first microphone;

e) generating a first level output signal based on the first cardioid shape signal and adaptive weights output, the adaptive weights output being calculated based on the second cardioid shape signal;

f) detecting at least one speech region and a non-speech region of the first level output signal;

g) generating a second level output signal based on the second cardioid shape signal, and at least one of the speech regions and the non-speech regions of the first level output signal; and h) removing residuals of noise from the first level output signal based on the generated second level output signal.

Point 2. The method of point 1 further comprising applying a propagation delay in the second microphone signal and the first microphone signal to generate the delayed second microphone signal and the delayed first microphone signal respectively, the propagation delay being applied for a length of time equal to one sample.

Point 3. The method of point 1, wherein the adaptive weights output being determined by ratios of a cross-correlation Rxy between the first microphone and the second microphone, and an auto-correlation Ryy of the second microphone.

Point 4. The method of point 3 further comprising averaging the auto-correlation and the cross-correlation by using W opt, wherein W opt=R xy/R yy; R xy=α.R xy_prev+(1−α) R xy; and R yy=α.R yy_prev+(1−α) R yy.

Point 5. The method of point 1, wherein generating the second level output signal comprises at least one of:

determining weights to generate an output signal based on the second cardioid shape signal when the non-speech region of the first level output signal is detected, the output signal corresponds to the residuals of noise present in the first level output signal; and freezing adaptive weights calculations when the speech region of the first level output signal is detected.

Point 6. The method of point 1, wherein the residuals of noise being removed from the first level output signal by subtracting the generated second level output signal.

Point 7. A method for speech signal enhancement comprising:

receiving first microphone signal and second microphone signal from a front microphone and a back microphone respectively;

obtaining a first cardioid shape signal and a second cardioid shape signal based on a delayed second microphone signal and a delayed first microphone signal respectively;

obtaining cardioid shape output signal by processing the first cardioid shape signal and the second cardioid shape signal; further obtaining the cardioid shape output signal by: generating a first level output signal by calculating adaptive weights as a ratios of a cross-correlation Rxy, between the first microphone and the second microphone, and an auto-correlation Ryy of the second microphone;

updating the adaptive weights to generate a second level output signal based on the second cardioid shape signal and the first level output signal, the second level output signal being generated when a non-speech region of the first level output signal is detected; and removing residuals of noise from the first level output signal by subtracting the second level output signal from the first level output signal.

Point 8. The method of point 7, wherein the delayed second microphone signal and the delayed first microphone signal being obtained by applying a propagation delay in the second microphone signal and the first microphone signal respectively, the propagation delay being applied for a length of time equals to one sample.

Point 9. The method of point 7, wherein the first level output signal is generated based on the first cardioid shape signal and the calculated adaptive weights, the adaptive weights being calculated based on the second cardioid shape signal.

Point 10. The method of point 9 further comprising freezing the adaptive weights when a speech region of the first level output signals is detected.

Point 11. The method of point 10 further comprising averaging the auto-correlation and the cross-correlation by using W opt, wherein W opt=R xy/R yy; R xy=α.R xy_prev+(1−α) R xy; and R yy=α.R yy_prev+(1−α) R yy.

Point 12. The method of point 11 further comprising detecting at least one of a speech region and a non-speech region of the first level output signal.

Point 13. The method of point 12, wherein the first cardioid shape signal being obtained by subtracting the delayed second microphone signal from the first microphone signal.

Point 14. The method of point 13, wherein the second cardioid shape signal being obtained by subtracting the second microphone signal from the delayed first microphone signal.

Point 15. A system for speech enhancement comprising:

a first microphone and a second microphone for providing a first microphone signal and a second microphone signal respectively;

means for obtaining a cardioid shape output signal by processing the first microphone signal and the second microphone signal;

delay elements for obtaining a delayed first microphone signal and a delayed second microphone signal, the delayed second microphone signal being subtracted from the first microphone signal to obtain a first cardioid shape signal, the second microphone signal being subtracted from the delayed first microphone signal to obtain a second cardioid shape signal;

a first adaptive filter for calculating adaptive weights as a ratios of a cross-correlation, between the first microphone and the second microphone, and an auto-correlation of the second microphone, the adaptive weights being utilized to generate a first level output signal based on the first cardioid shape signal;

a voice activity detector to detect at least one of a speech region and a non-speech region of the first level output signal; and a second adaptive filter for generating a second level output signal based on the second cardioid shape signal and detected at least one of the speech region and the non-speech region of the first level output signal, wherein the second level output signal being utilized to remove residuals of noise from the first level output signal to obtain the cardioid shape output signal for speech enhancement.

Point 16. The system of point 15, wherein the voice activity detector assumes an OFF position and an ON position on detecting the non-speech region and the speech region, respectively, of the first level output signal.

Point 17. The system of point 16, wherein the second adaptive filter generates the second level of output signal by updating the adaptive weights based on the second cardioid shape signal, when the non-speech region of the first level output signal is detected.

Point 18. The system of point 17, wherein the voice activity detector is further configured to freeze the adaptive weights, when the speech region of the first level output signals is detected.

Point 19. The system of point 18, wherein the delay elements are configured to apply a propagation delay in the second microphone signal and the first microphone signal to generate the delayed second microphone signal and the delayed first microphone signal respectively, the propagation delay being applied for a length of time equal to one sample.

Point 20. The system of point 19, wherein the voice activity detector is configured to control the first adaptive filter and the second adaptive filter by detecting the speech region and the non-speech region of the first level output signal.

What is claimed is:

1. A method of improving signal quality in a voice communication system, the method comprising:

a) receiving one or more buffers of sound samples from a first microphone and a second microphone, resulting in a first microphone signal and a second microphone signal;

b) processing the first microphone signal and the second microphone signal to obtain a cardioid shape output signal;

c) obtaining a first cardioid shape signal by subtracting a delayed second microphone signal from the first microphone signal, the delayed second microphone signal obtained from the second microphone;

d) obtaining a second cardioid shape signal by subtracting the second microphone signal from a delayed first microphone signal, the delayed first microphone signal obtained from the first microphone;

e) generating a first level output signal based on the first cardioid shape signal and adaptive weights output, the adaptive weights output being calculated based on the second cardioid shape signal;

f) detecting at least one speech region and a non-speech region of the first level output signal;

g) generating a second level output signal based on the second cardioid shape signal, and at least one of the speech regions and the non-speech regions of the first level output signal; and h) removing residuals of noise from the first level output signal based on the generated second level output signal.

2. The method of claim 1 further comprising applying a propagation delay in the second microphone signal and the first microphone signal to generate the delayed second microphone signal and the delayed first microphone signal respectively, the propagation delay being applied for a length of time equal to one sample.

3. The method of claim 1, wherein the adaptive weights output being determined by ratios of a cross-correlation Rxy between the first microphone and the second microphone, and an auto-correlation Ryy of the second microphone.

4. The method of claim 3 further comprising averaging the auto-correlation and the cross-correlation by using W opt, wherein W opt=R xy/R yy; R xy=$\alpha$.R xy_prev+(1−$\alpha$) R xy; and R yy=$\alpha$.R yy_prev+(1−$\alpha$) R yy.

5. The method of claim 1, wherein generating the second level output signal comprises at least one of:

determining weights to generate an output signal based on the second cardioid shape signal when the non-speech region of the first level output signal is detected, the output signal corresponds to the residuals of noise present in the first level output signal; and freezing adaptive weights calculations when the speech region of the first level output signal is detected.

6. The method of claim 1, wherein the residuals of noise being removed from the first level output signal by subtracting the generated second level output signal.

7. A method for speech signal enhancement comprising:

receiving first microphone signal and second microphone signal from a front microphone and a back microphone respectively;

obtaining a first cardioid shape signal and a second cardioid shape signal based on a delayed second microphone signal and a delayed first microphone signal respectively;

obtaining cardioid shape output signal by processing the first cardioid shape signal and the second cardioid shape signal;

further obtaining the cardioid shape output signal by:

generating a first level output signal by calculating adaptive weights as a ratios of a cross-correlation Rxy, between the first microphone and the second microphone, and an auto-correlation Ryy of the second microphone;

updating the adaptive weights to generate a second level output signal based on the second cardioid shape signal and the first level output signal, the second level output signal being generated when a non-speech region of the first level output signal is detected; and removing residuals of noise from the first level output signal by subtracting the second level output signal from the first level output signal.

8. The method of claim 7, wherein the delayed second microphone signal and the delayed first microphone signal being obtained by applying a propagation delay in the second microphone signal and the first microphone signal respectively, the propagation delay being applied for a length of time equals to one sample.

9. The method of claim 7, wherein the first level output signal is generated based on the first cardioid shape signal and the calculated adaptive weights, the adaptive weights being calculated based on the second cardioid shape signal.

10. The method of claim 9 further comprising freezing the adaptive weights when a speech region of the first level output signals is detected.

11. The method of claim 10 further comprising averaging the auto-correlation and the cross-correlation by using W opt, wherein W opt=R xy/R yy; R xy=$\alpha$.R xy_prev+(1−$\alpha$) R xy; and R yy=$\alpha$.R yy_prev+(1−$\alpha$) R yy.

12. The method of claim 11 further comprising detecting at least one of a speech region and a non-speech region of the first level output signal.

13. The method of claim 12, wherein the first cardioid shape signal being obtained by subtracting the delayed second microphone signal from the first microphone signal.

14. The method of claim 13, wherein the second cardioid shape signal being obtained by subtracting the second microphone signal from the delayed first microphone signal.

15. A system for speech enhancement comprising:

a first microphone and a second microphone for providing a first microphone signal and a second microphone signal respectively;

means for obtaining a cardioid shape output signal by processing the first microphone signal and the second microphone signal;

delay elements for obtaining a delayed first microphone signal and a delayed second microphone signal, the delayed second microphone signal being subtracted from the first microphone signal to obtain a first cardioid shape signal, the second microphone signal being subtracted from the delayed first microphone signal to obtain a second cardioid shape signal;

a first adaptive filter for calculating adaptive weights as a ratios of a cross-correlation, between the first microphone and the second microphone, and an auto-correlation of the second microphone, the adaptive weights being utilized to generate a first level output signal based on the first cardioid shape signal;

a voice activity detector to detect at least one of a speech region and a non-speech region of the first level output signal; and a second adaptive filter for generating a second level output signal based on the second cardioid shape signal and detected at least one of the speech region and the non-speech region of the first level output signal, wherein the second level output signal being utilized to remove residuals of noise from the first level output signal to obtain the cardioid shape output signal for speech enhancement;

wherein the voice activity detector assumes an OFF position and an ON position upon detecting the non-speech region and the speech region, respectively, of the first level of output signal;

wherein the second adaptive filter generates the second level of output signal by updating the adaptive weights based on the second cardiod shape signal, when the non-speech region of the first level output signal is detected.

16. The system of claim 15, wherein the voice activity detector is further configured to freeze the adaptive weights, when the speech region of the first level output signals is detected.

17. The system of claim 16, wherein the delay elements are configured to apply a propagation delay in the second microphone signal and the first microphone signal to generate the delayed second microphone signal and the delayed first microphone signal respectively, the propagation delay being applied for a length of time equal to one sample.

18. The system of claim 17, wherein the voice activity detector is configured to control the first adaptive filter and the second adaptive filter by detecting the speech region and the non-speech region of the first level output signal.

* * * * *